United States Patent
Wada

(10) Patent No.: US 9,566,003 B2
(45) Date of Patent: Feb. 14, 2017

(54) OPHTHALMOLOGIC APPARATUS AND METHOD THEREOF

(71) Applicant: CANON KABUSHIKI KAISHA, Tokyo (JP)

(72) Inventor: Manabu Wada, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 390 days.

(21) Appl. No.: 14/065,625

(22) Filed: Oct. 29, 2013

(65) Prior Publication Data

US 2014/0132925 A1    May 15, 2014

(30) Foreign Application Priority Data

Nov. 9, 2012 (JP) .................. 2012-247030

(51) Int. Cl.
*A61B 3/14* (2006.01)
*A61B 3/15* (2006.01)

(52) U.S. Cl.
CPC ..................... *A61B 3/152* (2013.01)

(58) Field of Classification Search
USPC ............... 351/200, 205, 206, 208–211, 221, 222, 351/243–246, 203, 204, 216, 233, 237
See application file for complete search history.

(56) References Cited

U.S. PATENT DOCUMENTS

| 7,695,139 B2 * | 4/2010 | Ishikura ................ 351/208 |
| 7,929,797 B2 | 4/2011 | Matsuzaka | |
| 2007/0146636 A1 | 6/2007 | Ishikura | |
| 2007/0279696 A1 | 12/2007 | Matsuzaka | |
| 2011/0051087 A1 | 3/2011 | Inoue et al. | |
| 2011/0299034 A1 * | 12/2011 | Walsh et al. ................ 351/206 |
| 2012/0218518 A1 | 8/2012 | Wada | |

FOREIGN PATENT DOCUMENTS

| CN | 1989894 A | 7/2007 |
| JP | 62-34530 A | 2/1987 |
| JP | 8-275921 A | 10/1996 |
| JP | 2001-046340 A | 2/2001 |
| JP | 2001-120503 A | 5/2001 |
| JP | 3569026 B2 | 9/2004 |
| JP | 2004-313455 A | 11/2004 |
| JP | 2007-323509 A | 12/2007 |

OTHER PUBLICATIONS

Apr. 15, 2015 Chinese Official Action in Chinese Patent Appln. No. 201310549549.1.
Dec. 15, 2015 Chinese Official Action in Chinese Patent Appln. No. 201310549549.1.

* cited by examiner

*Primary Examiner* — Joseph P Martinez
*Assistant Examiner* — Brandi Thomas
(74) *Attorney, Agent, or Firm* — Fitzpatrick, Cella, Harper & Scinto

(57) ABSTRACT

In order to detect a position alignment state between an apparatus and an eye to be inspected in a working distance direction with high precision at a high speed in the apparatus side, an ophthalmologic apparatus is disclosed. The position alignment state between the eye to be inspected and the apparatus in the working distance direction is detected by evaluating a contrast of an index image that is obtained as a reflection image of an index projected onto an anterior ocular segment, and a contrast of the index image is evaluated using a ratio or a difference between pixel numbers of the index image in at least two or more gray scale values.

14 Claims, 3 Drawing Sheets

OPHTHALMOLOGIC APPARATUS AND METHOD THEREOF

BACKGROUND OF THE INVENTION

Field of the Invention

The present invention relates to an ophthalmologic apparatus and a method thereof.

Description of the Related Art

In the related art, in an ophthalmologic photographing apparatus represented as a non-mydriatic fundus camera, photographing is performed such that an operator performs precise position alignment, between an apparatus and an eye to be inspected in horizontal and vertical directions and a working distance (back and forth) direction while viewing an observation image captured by an image pickup element. This precise position alignment in horizontal and vertical directions and the working distance (back and forth) direction is performed such that an index projected onto an anterior ocular segment of the eye to be inspected is captured by the image pickup element, and the alignment is performed with reference to the captured index image.

Here, focusing on position alignment, in the working distance direction, JP S62-34530 A discloses a fact that, when the working distance between the apparatus and the eye to be inspected is appropriately positioned, a contrast of the index image is maximized. Meanwhile, when the working distance between the apparatus and the eye to be inspected is not appropriately positioned, a contrast of the index image decreases. An operator completes the position alignment in the working distance direction by manipulating the apparatus back and forth such that the contrast of the index image is maximized.

Recently, there has proposed an ophthalmologic photographing apparatus in which a position alignment state between the apparatus and the eye to be inspected in horizontal and vertical directions and a working distance (back and forth) direction is detected in an apparatus side as disclosed in JP 3569026 B1.

As a first problem, in the ophthalmologic photographing apparatus disclosed in JP 3569026 B1, when the position alignment state between the apparatus and the eye to be inspected in horizontal and vertical directions and a working distance (back and forth) direction is not accurately detected in the apparatus side, a flare from a cornea or a lens occasionally enters a photographing image. In addition, as a second problem, since a time for which the eye to be inspected can maintain a fixation state is significantly short, it is necessary to detect the position alignment state between the apparatus and the eye to be inspected in horizontal and vertical directions and working distance (back and forth) direction at a high speed.

In order to address the two problems described above, in the apparatus side, it is necessary to detect the position alignment state between the apparatus and the eye to be inspected in horizontal and vertical directions and a working distance direction with high precision at a high speed.

SUMMARY OF THE INVENTION

In view of the aforementioned problems, the in provides an ophthalmologic photographing apparatus and an ophthalmologic photographing method capable of detecting a position alignment state in a working distance direction with high precision at a high speed.

In order to address the problems described above, an ophthalmologic photographing apparatus according to the present invention includes:

an index projecting unit configured to project an index onto an anterior ocular segment of an eye to be inspected;

an image pickup element configured to capture reflection from the anterior ocular segment for the index projected by the index projecting unit;

a working distance detecting unit configured to detect a position alignment state between the eye to be inspected and an apparatus in a working distance direction from the index image captured by the image pickup element; and a contrast evaluation unit configured to evaluate a contrast of the index image, wherein the working distance detecting unit detects an alignment state between the eye to be inspected and the apparatus based on an evaluation result of the contrast evaluation unit.

In order to address the problems described above, an ophthalmologic imaging method according to the present invention includes steps of:

index projecting steps for projecting an index onto an anterior ocular segment of an eye to be inspected;

photographic capturing step for capturing reflection from the anterior ocular segment of the index projected in the index projecting step;

working distance detecting step for detecting a position alignment state between the eye to be inspected and an apparatus in a working distance direction from an index image captured in the photographic capturing step; and contrast evaluation process step for evaluating contrast of the index image, wherein, in the working distance detecting step, a position alignment state between the eye to be inspected and the apparatus in the working distance direction is detected based on an evaluation result of the contrast evaluation step.

According to the invention, it is possible to provide an ophthalmologic photographing apparatus and an ophthalmologic photographing method capable of detecting the position alignment state between the apparatus and the eye to be inspected in the working distance direction in the apparatus side with high precision at a high speed.

Further features of the present invention will become apparent from the following description of exemplary embodiments with reference to the attached drawings.

BRIEF DESCRIPTION OF TEE DRAWINGS

DESCRIPTION OF THE EMBODIMENTS

Preferred embodiments of the present invention will now be described in detail in accordance with the accompanying drawings.

First Embodiment

Figure 1:
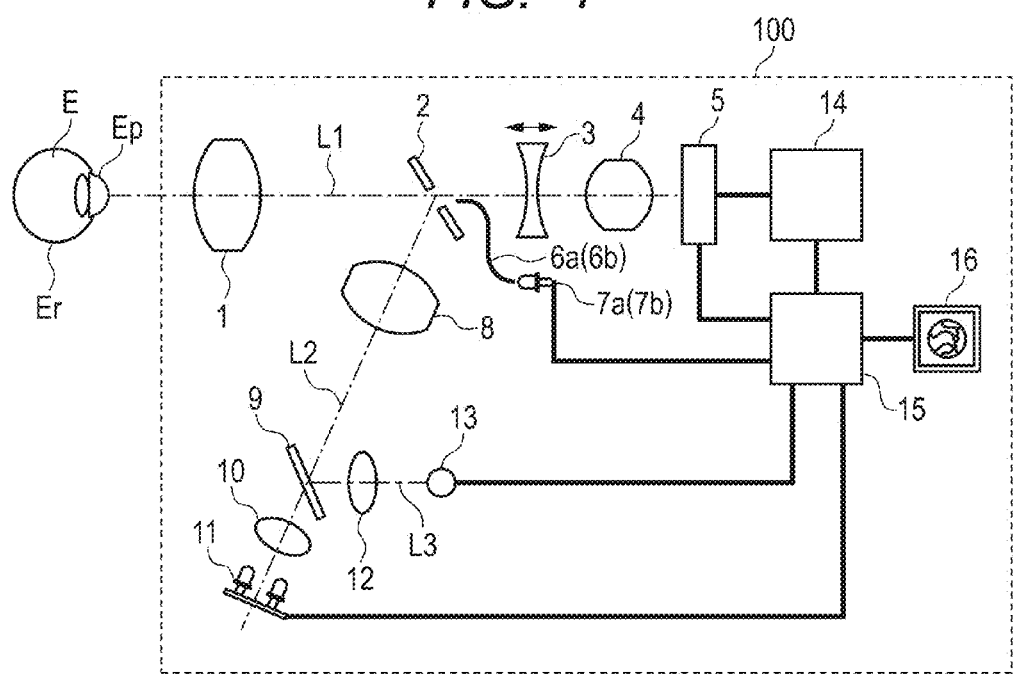
FIG. 1 is a diagram illustrating a configuration of a non-mydriatic fundus camera according to a embodiment of the invention.

Hereinafter, a first exemplary embodiment of the invention will be described with reference to the accompanying drawings. FIG. 1 is a diagram illustrating a configuration of a non-mydriatic fundus camera 100 as an exemplary ophthalmologic photographing apparatus.

First, the configuration of the non-mydriatic fundus camera 100 will be described.

On an optical axis L1 facing a fundus Er of an eye to be inspected E, an objective lens 1, a perforated mirror 2, a focus lens 3, an image forming lens 4, and an image pickup element are sequentially provided. These components constitute a fundus photographing optical system for the eye to be inspected E.

Meanwhile, on an optical axis L2 in a reflection direction of the perforated mirror 2, a lens 8, a dichroic mirror 9, a condenser lens 10, and an observation light source 11 are arranged. In addition, on an optical axis L3 in a reflection direction of the dichroic mirror 9, condenser lens 12 and a photographing light source 13 are arranged. These components on the optical axes L2 and L3 constitute a fundus illumination optical system.

The dichroic mirror 9 transmits a wavelength band of the observation light source 11 and reflects a wavelength band of the photographing light source 13. The observation light source 11 is a light source that includes a plurality of light-emitting diodes (LEDs) and emits light having an infrared range wavelength to the eye to be inspected. The photographing light source 13 is a light source that emits light having a visible range wavelength to the fundus Er.

In the vicinity of the perforated mirror 2, an index light source 7a and a light guide 6a for projecting an position alignment index in a working distance direction onto an anterior ocular segment of the eye to be inspected are arranged. In addition, a light guide 6b and an index light source 7b are arranged in a paper rear direction opposite to the light guide 6a and the index light source 7a with respect to the optical axis L1. Reflection light from the anterior ocular segment of the eye to be inspected of the index projected by the light guides 6a and 6b, and the index light sources 7a and 7b, has the maximum contrast on the image pickup element 5 when a working distance between the eye to be inspected E and the non-mydriatic fundus camera 100 is appropriately positioned. That is, a light emission position, serving as en index, from the light guides 6a and 6b is positioned adjacently to or in the vicinity of the optical axis of the reflection light reaching the image pickup element 5 from the anterior ocular segment, where light can be emitted from an aperture of the perforated mirror 2, so that a finite-distance index is projected onto the anterior ocular segment.

A working distance detecting section 14, a fundus camera control section 15, and a display portion 16 are provided inside the non-mydriatic fundus camera 100. Specifically, the working distance detecting section 14 is connected to the image pickup element 5 and the fundus camera control section 15. The working distance detecting section 14 detects a position alignment state between the non-mydriatic fundus camera 100 and the eye to be inspected in at working distance direction using an index image reflected from the anterior ocular segment of the eye to be inspected of index light sources 7a and 7b and captured by the image pickup element 5 and informs the detection result to the fundus camera control section 15.

The fundus camera control section 15 is connected to the index light sources 7a and 7b, the observation light source 11, the photographing light source 13, the working distance detecting section 14, and the display portion 16. The fundus camera control section 15 performs light emission control of the index light sources 7a and 7h, the observation light source 11, and the photographing light source 13, displays images captured by the image pickup element 5 on the display portion 16, and displays, on the display portion 16, the detection result of the position alignment state between the non-mydriatic fundus camera 100 and the eye to be inspected in the working distance direction informed from the working distance detecting section 14.

In the configuration of the aforementioned non-mydriatic fundus camera 100, operations from observation to photographing will be described.

First, observation will be described.

Figure 2:
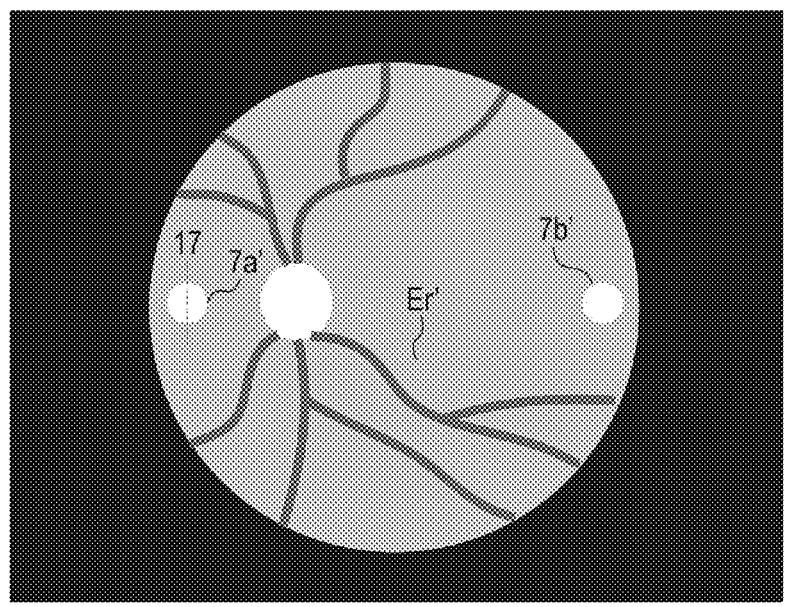
FIG. 2 is a diagram illustrating a fundus observation image and an index image displayed on a display section of the non-mydriatic fundus camera illustrated in FIG. 1.

As an operator positions the eye to be inspected E in front of the objective lens 1, the fundus camera control section 15 causes the observation light source 11 to emit light. This observation illumination light passes through the fundus illumination optical system reaching the objective lens 1 from the observation light source 11 and illuminates the fundus Er via a pupil Ep of the eye to be inspected E. Reflection light emitted from the observation light source 11 and reflected from the fundus Er passes through a fundus photographing optical system including the objective lens 1, the perforated mirror 2, the focus lens 3, and the image forming lens 4 and reaches the image pickup element 5. A fundus observation image captured by the image pickup element 5 is displayed on the display portion 16 by the fundus camera control section 15. At the same time, the fundus camera control section 15 causes the index light sources 7a and 7b to emit light and projects the position alignment index in the working distance direction onto the anterior ocular segment of the eye to be inspected via an optical path from the light guides 6a and 6b to the objective lens 1. Such a configuration corresponds to an index projecting unit according to the invention. The reflection light from the anterior ocular segment of the eye to be inspected of the projected index passes through the fundus photographing optical system including the objective lens 1, the perforated mirror 2, the focus lens 3, and the image forming lens 4 and reaches the image pickup element 5. The index image captured by the image pickup element 5 is displayed on the display portion 16 by the fundus camera control section 15. FIG. 2 illustrates the fundus observation image and the index image displayed on the display portion 16. In FIG. 2, the fundus observation image is denoted by Er', and the index images are denoted by 7a' and 7b'.

An operator manipulates an operation stick (not illustrated) to move the non-mydriatic fundus camera 100 up, down, left, right, back, and forth while viewing the fundus observation image Er' and the index images 7a' and 7b' displayed on the display portion 16, so that position alignment between the eye to be inspected E and the non-mydriatic fundus camera 100 is performed in horizontal, and vertical directions and a working distance direction. In the position alignment of the working distance direction, the detection result of the position alignment state between the non-mydriatic fundus camera 100 and the eye to be inspected in the working distance direction informed from the working distance detecting section 14 is displayed on the display portion 16. Therefore, an operator moves the non-mydriatic fundus camera 100 back and forth such that the contrasts of the index images 7a1 and 7b' are maximized while viewing an evaluation result. In addition, an operator performs focus adjustment by adjusting the focus lens 3.

Next, a photographing sequence will be described. As described above, when precise position alignment between the eye to be inspected E and the non-mydriatic fundus camera 100 and the focus adjustment are completed, an operator performs photographing by manipulating a photographing start switch (not illustrated).

As the photographing start switch is manipulated, the fundus camera control section 15 causes the photographing light source 13 to emit light. Photographing illumination light emitted from the photographing light source 13 passes through the fundus illumination optical system from the photographing light source 13 to the objective lens 1 and illuminates the fundus Er. Reflection light from the fundus Er illuminated from the photographing light source 13 passes through the fundus photographing optical system including the objective lens 1, the perforated mirror 2, the focus lens and the image forming lens 4 and reaches the image pickup element 5. The fundus camera control section 15 performs a gamma curve calculation and a color conversion operation for the fundus photographing image captured by the image pickup element 5, and the result is displayed on the display portion 16.

Figure 3:
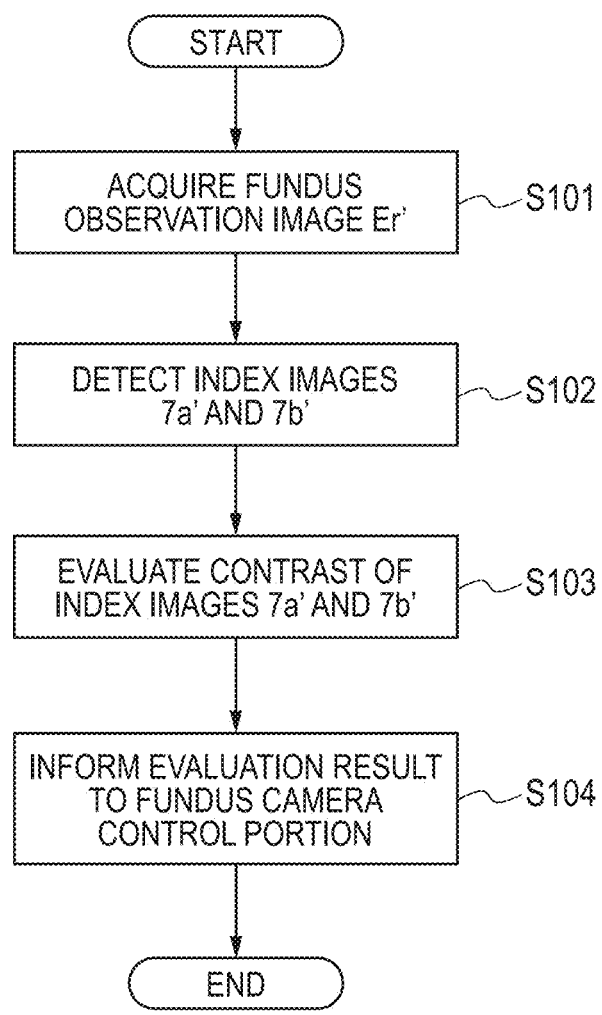
FIG. 3 is a flowchart illustrating operations of working distance detecting section of the non-mydriatic fundus camera in FIG. 1.

Next, the working distance detecting section 14 as a characteristic of the invention will be described in detail. A description has been made by assuming that the working distance detecting section 14 detects the position alignment state between the non-mydriatic fundus camera 100 and the eye to be inspected E in the working distance direction. Now, a specific detection operation will be described with reference to the flowchart of FIG. 3.

First, when the fundus observation image Er' is captured by the image pickup element the working distance detecting section 14 acquires the fundus observation image Er' (step 101).

Then, the working distance detecting section 14 detects the index image 7a' or 7b' from the fundus observation image Er' acquired in step 101. In this case, either or both of the index images 7a' and 7b' may be detected. In this embodiment, a case where the index image 7a' is detected will be described by way of example (step 102).

Figure 4:
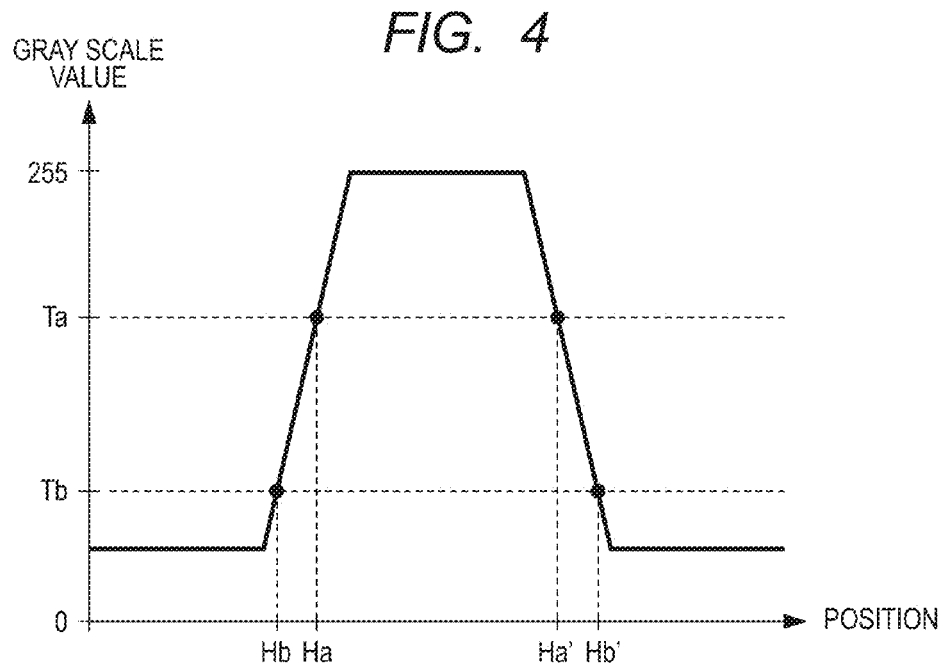
FIG. 4 is a diagram illustrating a change of a gray scale value on a dotted line in FIG. 2 in an index image when position alignment between the non-mydriatic fundus camera in FIG. 1 and an eye to be inspected in working distance direction is completed.
Figure 5:
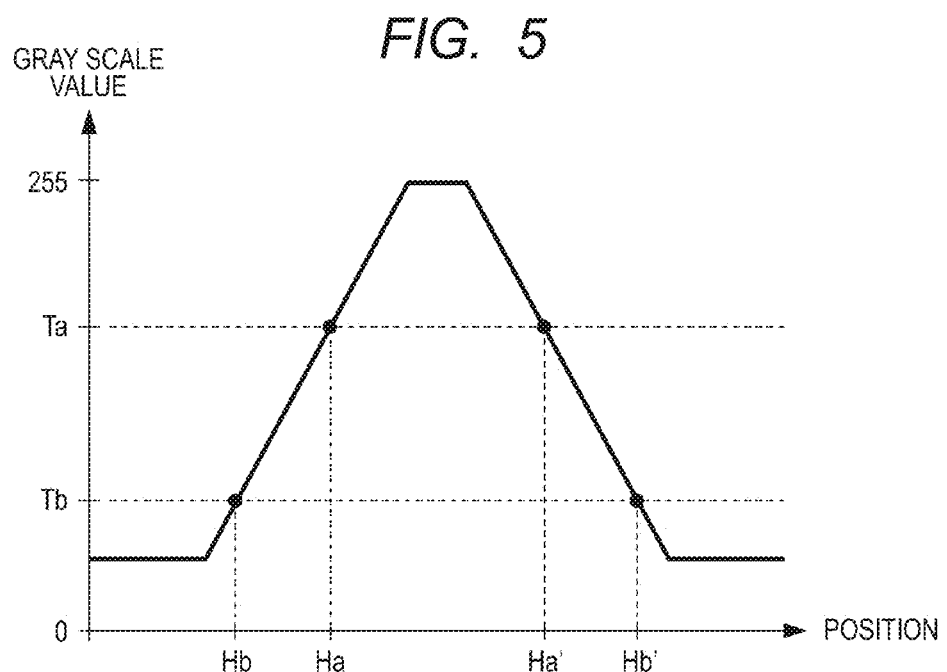
FIG. 5 is a diagram illustrating a change of a gray scale value on a dotted line in FIG. 2 in an index image when position alignment between the non-mydriatic camera in FIG. 1 and the eye to be inspected in the working distance direction is not completed.

Then, the working distance detecting section 14 evaluates the contrast of the index image 7a' (step 103). Contrast evaluation is performed by a component serving as a contrast evaluation unit in the working distance detecting section 14. The contrast evaluation of the index image 7a' will be described with reference to FIGS. 4 and 5. FIGS. 4 and 5 illustrate a gray scale value on the dotted line 17 of the index image 7a' of FIG. 2. FIG. 4 illustrates a state that the position alignment between non-mydriatic fundus camera 100 and the eye to be inspected in the working distance direction is completed, that is, a state that the contrast of the index image 7a' is maximized. Meanwhile, FIG. 5 illustrates a state that the position alignment between the non-mydriatic fundus camera 100 and the eye to be inspected in the working distance direction is not completed, that is, the contrast of the index image 7a' is not maximized.

Furthermore, Ha, Ha', Hb, and Hb' of FIGS. 4 and 5 denote coordinates in the gray scale values of Ta and Tb on the dotted line 17 of the index image 7a'. More specifically, Ta denotes a gray scale value within a dynamic range of the index image 7a', and Tb denotes a gray scale value different from Ta within the dynamic range of the index image 7a'. In addition, Ha denotes a coordinate position having a gray scale value of Ta on the dotted line 17 of the index image 7a', and Ha' denotes a coordinate position having a gray scale value of Ta on the dotted line 17 of the index image 7a'. HAS denotes a coordinate position having a gray scale value of Tb on the dotted line 17 of the index image 7a'. Hb' denotes a coordinate position having a gray scale value of Tb on the dotted line 17 of the index image 7a'. Ta and Tb may be different gray scale values within the dynamic range of the index image 7a'.

Then, a pixel number of the index image in Ta is represented by Ha'−Ha, and a pixel number of the index image 7a' in Tb is represented by Hb'−Hb. A ratio thereof cam be expressed as the following Equation 1, which is referred to as a contrast evaluation value or the index image.

Equation 1

$$\text{contrast evaluation value of index image} = \frac{Ha' - Ha}{Hb' - Hb} \qquad \text{Equation 1}$$

Here, when Equation 1 is applied to the states of FIGS. 4 and 5, the following facts are recognized. For example, as illustrated in FIG. 4, when the position alignment between the non-mydriatic fundus camera 100 and the eye to be inspected in the working distance direction is completed, that is, when the contrast of the index image 7a' is maximized, Ha'−Ha is close to Hb'−Hb. Therefore, the contrast evaluation value of the index image given by Equation 1 becomes close to zero. That is, when the contrast evaluation unit presents the maximum contrast, the working distance detecting section detects that the position alignment in the working distance direction is appropriately performed. Meanwhile, as illustrated in FIG. 5, when the position alignment between the non-mydriatic fundus camera 100 and the eye to be inspected in the working distance direction is not completed, that is, when the contrast of the index image 7a' is not maximized, Ha'−Ha is smaller than Hb'−Hb. Therefore, the contrast evaluation value of the index image given by Equation 1 becomes close to zero. In this way, it is recognized that the contrast of the index image can be evaluated by calculating the ratio of the pixel number between two gray scale values.

Finally, the working distance detecting section informs the contrast evaluation result of the index image calculated in step 103 to the fundus camera control section 15 (step 104). Although the contrast of the index image is evaluated using Equation 1 in this embodiment, the following Equation 2 may also be used.

Equation 2

$$\text{contrast evaluation value of index image} = (Hb' - Hb) - (Ha' - Ha) \qquad \text{Equation 2}$$

For example, as illustrated in FIG. 4, when the position alignment between the non-mydriatic fundus camera 100 and the eye to be inspected in the working distance direction is completed, that is, when the contrast of the index image 7a' is maximized, Ha'−Ha is close to Therefore, the contrast evaluation value of the index image given by Equation 2 becomes close to zero. Meanwhile, as illustrated in FIG. 5, when the position alignment between the non-mydriatic fundus camera 100 and the eye to be inspected in the working distance direction is not completed, that is, when the contrast of the index image 7a' is not maximized, Ha'−Ha is smaller than Hb'–Hb. Therefore, the contrast evaluation value of the index image given by Equation 2 becomes apart from zero.

Although the contrast of the dotted line 17 of the index image in FIG. 2, that is in one line in a longitudinal direction of the image is evaluated in this embodiment by way of example, the contrast of the index image may be evaluated in a two-dimensional direction (horizontal and vertical, directions) of the image. Specifically, calculation may be performed such that Ha'–Ha calculated in step 103 is replaced with a pixel, number of the index image 7a' in a two-dimensional direction in Ta, and Hb'–Hb is replaced with a pixel number of the index image 7a' in a two-dimensional direction in Tb.

Further, although the contrast of the index image is evaluated using the ratio of the pixel number between two gray scale values Ta and Tb in this embodiment, the contrast of the index image may also be evaluated using at least two or more gray scale values. If at least two or more gray scale values are used, the contrast of the index image can be evaluated using a plurality of gray scale values. Therefore, it is possible to detect the position alignment state between the apparatus and the eye to be inspected in the working distance direction with higher precision. In addition, it is also possible to evaluate the contrast using a difference of the pixel number rather than a ratio thereof.

In a typical image processing technology, it is possible to simply and easily count the pixel number in a certain, gray scale value at a high speed. Therefore, according to the invention, it is possible to detect the position alignment state between the apparatus and the eye to be inspected in the working distance direction with high precision at a high speed.

Although the non-mydriatic fundus camera has been described in this embodiment by way of example, the invention may similarly apply to any ophthalmologic photographing apparatus if the contrast of the index image is changed depending the working distance position between the apparatus and the eye to be inspected.

Other Embodiments

The invention may also be implemented by performing the following process. Specifically, software (program) for implementing functionalities of the aforementioned embodiment is provided in a system or an apparatus via a network or various recording media, and a computer (a central processing unit (CPU) or a microprocessor unit (MPU)) in the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-247030, filed Nov. 9, 2012, which is hereby incorporated by reference herein in its entirety.

What is claimed is:

1. An ophthalmologic photographing apparatus comprising:
   an index projecting unit configured to project an index onto an anterior ocular segment of an eye to be inspected;
   an image pickup element configured to capture a common index image for alignment states in both (a) horizontal and vertical directions and (b) a working distance direction, the common index image corresponding to the index projected by the index projecting unit;
   a contrast evaluation unit configured to evaluate a contrast of the common index image;
   a detecting unit configured to detect a first alignment state between the eye to be inspected and an apparatus in the working distance direction based on the evaluated contrast of the common index image; and
   a control unit configured to control a display unit to display (1) a fundus image of the eye to be inspected, (2) the common index image, based on output of the image pickup element, and (3) a detection result of the first alignment state,
   wherein the common index image is also used for a second alignment state in the horizontal and vertical directions.

2. The ophthalmologic photographing apparatus according to claim 1, wherein the contrast evaluation unit evaluates the contrast using a ratio or a difference between pixel numbers of the index image in at least two or more gray scale values.

3. The ophthalmologic photographing apparatus according to claim 2, wherein the gray scale value is within a gray scale dynamic range of the index image.

4. The ophthalmologic photographing apparatus according to claim 1, wherein the detecting unit detects that the first alignment state is appropriate when the contrast evaluation unit presents an evaluation result that a contrast of the common index image is maximized.

5. The ophthalmologic photographing apparatus according to claim 1, wherein the index image projecting unit is provided adjacently to an optical axis along which reflection light from the anterior ocular segment reaches the image pickup element.

6. An ophthalmologic method comprising steps of:
   a photographic capturing step for capturing a common index image for alignment states in both (a) horizontal and vertical directions and (b) a working distance direction, the common index image corresponding to an index projected onto an anterior ocular segment of an eye to be inspected;
   a contrast evaluation step for evaluating a contrast of the common index image;
   a detecting step for detecting a first alignment state between the eye to be inspected and an apparatus in the working distance direction based on the evaluated contrast of the common index image; and
   a control step for controlling a display unit to display (1) a fundus image of the eye to be inspected, (2) the index image, based on output of the image pickup element, and (3) a detection result of the first alignment state,
   wherein the common index image is also used for a second alignment state in the horizontal and vertical directions.

7. The ophthalmologic method according to claim 6, wherein, in the contrast evaluation step, the contrast is evaluated using a ratio or a difference between pixel numbers of the index image in at least two or more gray scale values.

8. The ophthalmologic method according to claim 7, wherein the gray scale value is within a gray scale dynamic range of the index image.

9. The ophthalmologic method according to claim 6, wherein, in the detecting step, it is detected that the first alignment state is appropriate when an evaluation result that the contrast value of the common index image is maximized is presented in the contrast evaluation step.

10. A program that causes a computer to execute each of the steps of the ophthalmologic method according to claim 6.

11. An ophthalmologic photographing apparatus comprising:
- an index projecting unit configured to project an index onto an anterior ocular segment of an eye to be inspected;
- an image pickup element configured to capture a common index image for alignment states both (a) in horizontal and vertical directions and (b) a working distance direction, the common index image corresponding to the index projected by the index projecting unit; and
- a detecting unit configured to detect a first alignment state between the eye to be inspected and an apparatus in the working distance direction based on a contrast of the common index image,
- wherein the common index image is also used for a second alignment state in the horizontal and vertical directions.

12. The ophthalmologic photographing apparatus according to claim 11, further comprising a control unit configured to control a display unit to display the common index image and a detection result of the first alignment state.

13. An ophthalmologic method comprising steps of:
- a photographic capturing step for capturing a common index image for alignment states both (a) in horizontal and vertical directions and (b) a working distance direction, the common index image corresponding to an index projected onto an anterior ocular segment of an eye to be inspected; and
- a detecting step for detecting a first alignment state between the eye to be inspected and an apparatus in the working distance direction based on a contrast of the common index image,
- wherein the common index image is also used for a second alignment state in the horizontal and vertical directions.

14. A non-transitory tangible medium having recorded thereon a program that causes a computer to execute each of the steps of the ophthalmologic method according to claim 13.

* * * * *